United States Patent [19]

Fujinuma et al.

[11] Patent Number: 5,310,730

[45] Date of Patent: * May 10, 1994

[54] SKIN TREATMENT COMPOSITION

[75] Inventors: Yoshimori Fujinuma; Tomohisa Asahara, both of Yokohama; Satoru Akiu, Sagamihara; Yumiko Suzuki, Yokohama; Hideyuki Ichikawa, Yokohama; Yoshio Katsumura, Yokohama, all of Japan

[73] Assignee: Shiseido Company Ltd., Tokyo, Japan

[ * ] Notice: The portion of the term of this patent subsequent to Aug. 16, 2005 has been disclaimed.

[21] Appl. No.: 39,499

[22] Filed: Apr. 16, 1987

Related U.S. Application Data

[62] Division of Ser. No. 713,961, Mar. 20, 1985, Pat. No. 4,764,505.

[30] Foreign Application Priority Data

Sep. 7, 1983 [JP] Japan .................. 58-164815
Feb. 28, 1985 [JP] Japan .................. 60-37655

[51] Int. Cl.$^5$ ............................................. A61K 31/70
[52] U.S. Cl. ................................... 514/35; 514/25
[58] Field of Search .................................... 514/25, 35

[56] References Cited

U.S. PATENT DOCUMENTS 3,201,385 8/1965 Jarrett ........................... 536/18.6

OTHER PUBLICATIONS

Marty et al. *Chemical Abstracts* p. 449 vol. 85, 1976 No. 130442m.

*Primary Examiner*—Johnnie R. Brown
*Assistant Examiner*—Elli Peselev
*Attorney, Agent, or Firm*—Sprung Horn Kramer & Woods

[57] ABSTRACT

A skin treatment composition comprising at least one glycoside of hydroquinone having the general formula:

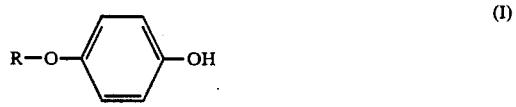

(I)

wherein R represents a pentose residue, a hexose residue, an amino sugar residue, or an uronic acid residue, or the methylated product thereof in a skin treatment base. This skin treatment composition can further contain at least one UV absorber. The hydroquinone glycoside (I) exhibits an excellent depigmentation effect and effectively suppresses skin irritation caused by the UV absorber.

3 Claims, 1 Drawing Sheet

SKIN TREATMENT COMPOSITION

This is a division of application Ser. No. 06/713,961, filed Mar. 20, 1985, now U.S. Pat. No. 4,764,505.

BACKGROUND OF THE INVENTION

1. Field of the Invention

The present invention relates to a skin treatment composition such as a cosmetic composition and a pharmaceutical preparation. More specifically, it relates to a skin treatment composition having a remarkably improved skin depigmentation effect and is very safe to use, as well as suppressing skin irritation caused by an ultraviolet (UV) absorber when the UV absorber is contained therein.

2. Description of the Related Art

Although the mechanisms of pigmentation such as melasma, chloasma, and the like in the skin are not fully understood, it is believed that a melanin pigment is formed and abnormally deposited in the skin due to hormone abnormalities and UV light irritation caused by sunlight. The above-mentioned pigmentation is generally treated by administering substances suppressing the formation of melanin. For example, vitamin C is administered in a large amount; glutathione or a similar compound is injected; or L-ascorbic acid, cysteine, or a similar compound is applied to localized areas in the form of an ointment, cream, or lotion.

In the United States and Europe, hydroquinone preparations are used as pharmaceuticals. These substances, however, suffer from various disadvantages. For example, L-ascorbic acid and its derivatives of higher fatty acids are disadvantageous in the stability thereof. In particular, when they are used in the presence of water, they cause unpreferable discoloration and an unpleasant odor. Thiol compounds such as glutathione and cysteine have irritant or unpleasant odors and, in addition, are susceptible to oxidation. Therefore, these compounds are generally not incorporated into skin treatment compositions such as cosmetic compositions.

Furthermore, the effects of the above-mentioned compounds for the intended treatment appear too weak, and the depigmentation effects are not satisfactory. On the other hand, although the depigmentation effects of hydroquinone on the skin are apparently recognized, the use of hydroquinone in skin treatment compositions is generally limited due to its contact allergenicity. Various attempts have been made to improve the disadvantage of hydroquinone and make it safer to use. For instance, the use of the mono esters of higher fatty acids of hydroquinone has been proposed to solve this problem. These esters, however, are easily hydrolyzed in the presence of esterases in vivo, and thus these esters are not necessarily safe to use.

Furthermore, conventional skin treatment compositions often contain UV absorbers to prevent the localized areas from sunlight, because melanization is promoted by the irradiation of sunlight. Nevertheless, the skin irritation due to the application of UV absorbers still occurs in some cases, depending on some type of UV absorbers used and individual differences in skin properties.

SUMMARY OF THE INVENTION

Accordingly, the objects of the present invention are to eliminate the above-mentioned disadvantages and to provide a skin treatment composition having a remarkably improved skin depigmentation effect without adversely effecting the skin.

Another object of the present invention is to provide a skin treatment composition having a remarkably improved skin depigmentation effect and suppressing skin irritation caused by a UV absorber when the UV absorber is contained in the composition, without having an adverse effect on the skin.

Other objects and advantages of the present invention will be apparent from the following description.

In accordance with the present invention, there is provided a skin treatment composition comprising at least one glycoside of hydroquinone having the general formula:

(I)

wherein R represents a pentose residue, a hexose residue, an amino sugar residue, or a uronic acid residue, or the methylated product thereof in a skin treatment base.

In accordance with the present invention, there is also provided a skin treatment composition comprising (i) at least one hydroquinone glycoside having the general formula (I) and (ii) at least one UV absorber in a skin treatment base.

BRIEF DESCRIPTION OF THE DRAWING

The present invention will be better understood from the description set forth below with reference to the accompanying drawing of FIG. 1, which graphically illustrates the stability, with the lapse of time, of arbutin (curve (1)) (i.e., the typical hydroquinone glucoside according to the present invention), hydroquinone (curve (2)), and hydroquinone monocaprylate (curve (3)). Also in FIG. 1, the changes of the absorbancy at 420 nm are shown with the lapse of time.

DESCRIPTION OF THE PREFERRED EMBODIMENTS

Figure 1:
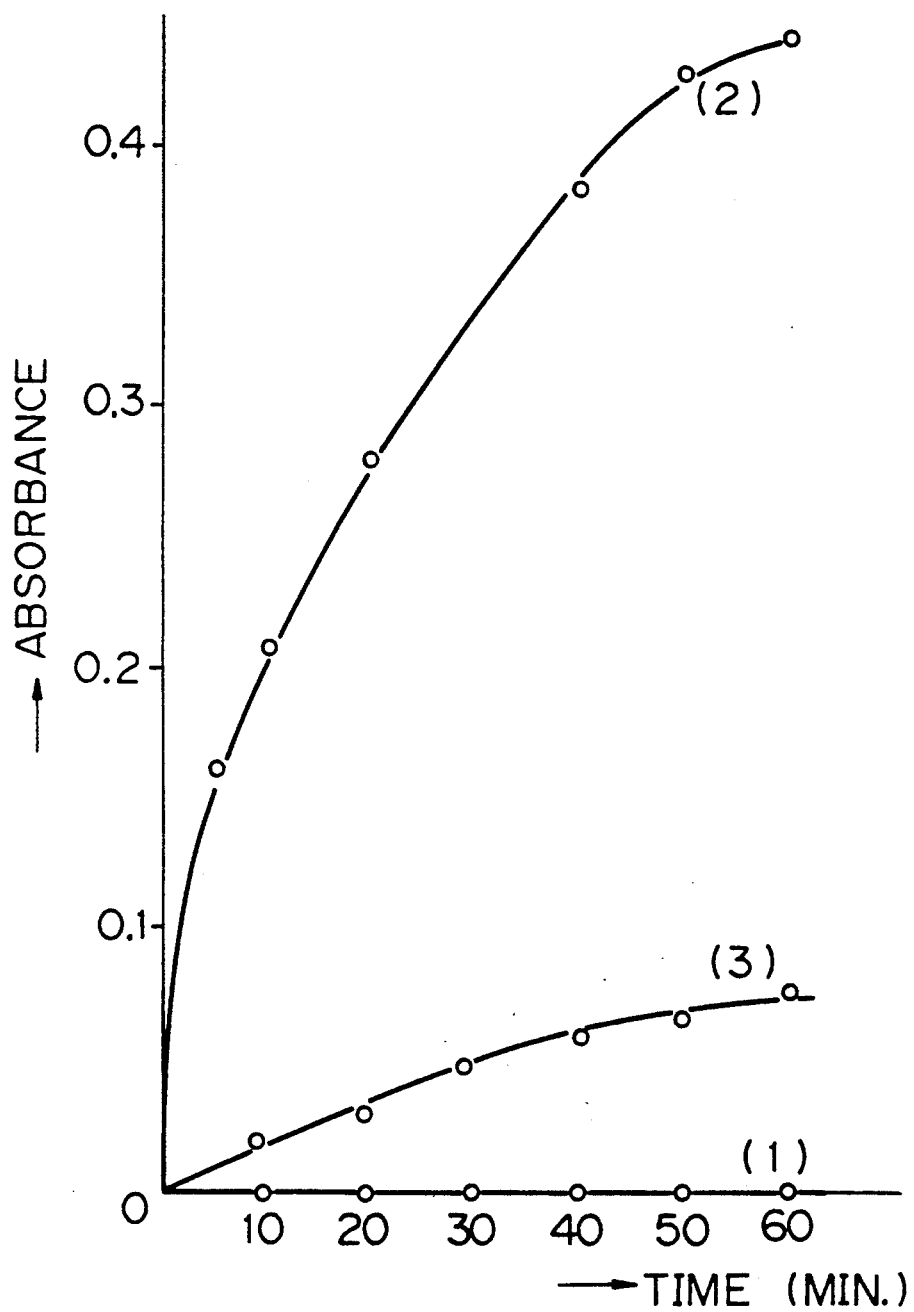

It has been found that the hydroquinone glycosides having the general formula (I) have an excellent safety margin and stability and exhibit excellent skin depigmentation effects superior to those of hydroquinone and the other derivatives thereof. It also has been found that the hydroquinone glycosides (I) effectively suppress skin irritation caused by UV absorbers, if present. Thus, the skin treatment compositions according to the present invention cause no substantial irritation to nor do they sensitize the skin and, therefore, can be continuously applied to the skin over a long period of time even at a relatively high concentration of the hydroquinone glycoside (I). Furthermore, when a UV absorber is used together with the hydroquinone glycoside (I), in a skin treatment composition, the skin irritation caused by the UV absorber, if present, can be effectively suppressed due to the presence of the hydroquinone glycoside (I).

The hydroquinone glycosides used in the present invention are those having the general formula (I). In the general formula (I), R represents pentose residues such as the residues of L-arabinose, D-arabinose, L-xylose, D-xylose, D-ribose, L-lyxose, and D-ribulose; hexose residues such as the residues of D-glucose, D-galactose, l-galactose, D-mannose, D-talose, D-fructose, L-sorbose, D-tagatose, and D-psicose; amino sugar residues such as the residues of D-glucosamine, D-galactosamine, sialic acid, amino uronic acid, and muramic acid; uronic acid residues such as the residues of D-glucuronic acid, D-galacturonic acid, D-mannuronic acid, L-iduronic acid, and L-guluronic acid; and the methylated products of the above-mentioned residues. Of these hydroquinone glycosides, the hydroquinone glycosides having D-glucose residues as the substituent R in the general formula (I), especially hydroquinone-$\beta$-D-glucoside (i.e., so-called "arbutin") which has a structure such that $\beta$-D-glucose is bonded to hydroquinone can be most preferably used in view of their skin depigmentation effects, availability, stability, safety, and suppression of the skin irritation caused by a UV absorber, if present. These hydroquinone glycosides can be used alone or in any mixture thereof in the skin treatment composition according to the present invention.

The above-mentioned hydroquinone glycosides also can be readily synthesized. For example, hydroquinone and acetylated sugar are refluxed, upon heating, in the presence of a catalyst such as phosphorus oxychloride, sulfuric acid, or thionyl chloride in a suitable solvent for several hours. The resultant reaction product is then subjected to a deacetylation reaction. Thus, the desired hydroquinone glycosides can be readily obtained. Furthermore, arbutin can be readily available in the market.

Although there is no critical limitation in the amount of the hydroquinone glycoside to be incorporated into the present skin treatment composition, the hydroquinone glycoside is preferably contained in the skin treatment composition in an amount of 0.1% to 30% by weight, more preferably 6% to 20% by weight. The use of too small an amount of the hydroquinone glycoside tends to decrease the desired skin depigmentation effect and the desired skin irritation suppression. Contrary to this, even when too large an amount of the hydroquinone glycoside is used in the present skin treatment composition, a further improvement in the desired skin depigmenting effects and skin irritating suppressing effects is not expected and, furthermore, formulation of the hydroquinone glycoside into the skin treatment composition becomes difficult from the practical point of view.

The UV absorbers usable in the second aspect of the present skin treatment composition are those conventionally used in skin treatment compositions.

Typical examples of such UV absorbers are:

(A) Para-amino benzoic acid type UV absorbers

Para-amino benzoic acid (i.e., "PABA" hereinbelow), monoglyceryl ester of PABA, ethyl ester of N,N-dipropoxy PABA, ethyl ester of N,N-diethoxy PABA, ethyl ester of N,N-dimethyl PABA, butyl ester of N,N-dimethyl PABA, amyl ester of N,N-dimethyl PABA, and octyl ester of N,N-diethyl PABA.

(B) Anthranilic acid type UV absorbers

Homomethyl N-acetyl anthranilate (C) Salicylic acid type UV absorbers

Amyl salicylate, menthyl salicylate, homomenthyl salicylate, octyl salicylate, phenyl salicylate, benzyl salicylate, and p-isopropanol phenyl salicylate.

(D) Cinnamic acid type UV absorbers

Octyl cinnamate, ethyl-4-isopropyl cinnamate, methyl-2,5-diisopropyl cinnamate, ethyl- 2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (or 2-ethylhexyl-p-methoxy cinnamate), 2-ethoxyethyl-p-methoxy cinnamate, cyclohexyl-p-methoxy cinnamate, ethyl-$\alpha$-cyano-$\beta$-phenyl cinnamate, 2-ethylhexyl-$\alpha$-cyano-$\beta$-phenyl cinnamate, and glyceryl mono 2-ethylhexanoyl diparamethoxy cinnamate.

(E) Benzophenone type UV absorbers 2,4-Dihydroxy benzophenone, 2,2'-dihydroxy-4-methoxy benzophenone, 2,2'-dihydroxy-4,4'-dimethoxy benzophenone, 2,2',4,4'-tetrahydroxy benzophenone, 2-hydroxy-4-methoxy benzophenone, 2-hydroxy-4-methoxy-4'-methyl benzophenone, 2-hydroxy-4-methoxy benzophenone-5-sulfonic acid salts, 4-phenyl benzophenone, 2-ethylhexyl-4'-phenyl benzophenone-2-carboxylate, 2-hydroxy-4-n-octoxy benzophenone, and 4-hydroxy-3-carboxy benzophenone.

(F) Other UV absorbers 3-(4'-methylbenzylidene)-d,l-camphor, 3-benzylidene-d,l-camphor, urocanic acid, ethyl urocanate, 2-phenyl-5-methylbenzoxazole, 2,2'-hydroxy-5-methylphenyl benzotriazole, 2-(2'-hydroxy-5'-t-octylphenyl) benzotriazole, 2-(2'-hydroxy-5'-methylphenyl) benzotriazole, dibenzalazine, dianisoyl methane, 4-methoxy-4'-t-butyl dibenzoylmethane, and 5-(3,3-dimethyl-2-norbornylidene)-3-pentane-2-one.

Although there is no critical amount of the UV absorber incorporated in the present skin treatment composition, the UV absorber is preferably used in the present skin treatment composition in an amount of 0.05% to 10% by weight, more preferably 0.5% to 8% by weight. The use of too small an amount of UV absorber tends to decrease the desired sunburn prevention effects on the skin and to offset the desired depigmentation effects of the hydroquinone glycosides. Contrary to this, the use of too large an amount of the UV absorber tends to adversely affect the stability of the skin treatment composition.

Furthermore, although a relative ratio of the amount of the hydroquinone glycoside in the skin treatment composition to the amount of the UV absorber in the skin treatment composition is not specifically limited, 0.1 to 60 parts by weight, based on one part by weight of the UV absorber, of the hydroquinone glycoside is preferably incorporated into the skin treatment composition to effectively eliminate the skin irritation caused by the UV absorber, if present.

The skin treatment bases usable in the present invention are those which are conventionally used in the formulation of skin treatment compositions. Examples of such treatment bases are: 0 to 35% by weight, preferably 1% to 35% by weight, of an alcohol, 0.01% to 5% by weight of a surfactant, 0 to 10% by weight, preferably 1% to 10% by weight, of oil, and the remainder of water in the case of liquid cream (or milk cream), lotion, and cream; oil or wax in the case of ointment; and 1% to 30% by weight of a film-forming agent, 0 to 35% by weight of an alcohol, and the remainder of water in the case of pack.

The skin treatment composition according to the present invention can optionally contain any conventional ingredients generally used in conventional skin treatment compositions, such as cosmetic compositions and pharmaceutical preparations. Examples of such ingredients are oils such as liquid paraffin, hydrocarbon, microcrystalline wax, vaseline, methylpolysiloxane, castor oil, squalane, and coconut oil; anti-oxidants such as butylated hydroxyanisole, butylhydroxytoluene, ethyl gallate, and tocopherol; surfactants such as sodium laurate, laurylpyridinium chloride, polyoxyethylene sorbitan monooleate, glyceryl monoarachate, sodium N-stearyl-N,N-dimethyl glycine, oleoyl hydrolyzed animal protein, and polyoxypropylene glyceryl ether phosphate; humectants such as glycerol, sodium 2-pyrrolidone-5-carboxylate, and sodium lactate; thickeners such as tragacanth gum, quince seed gum, xanthan gum, carboxyvinyl polymer, and bentnite; preservatives such as benzoic acid, alkyl p-hydroxybenzoates, dehydroacetic acid, and trichlorocarbanilide; coloring agents and pigments such as Acid Red, Rhodamine B, Violamin R, Orange SS, Naphthol, Yellow-S, Tartrazine, Alizarin, Cyanine Green F, Brilliant Blue FCF, Acid Violet, Carthamine, β-carotene, Red, Blue & Yellow Oxide of Iron, titanium dioxide, Yellow Iron Oxide, Cobalt Blue, Ultramarine Blue, Rose & Violet, tri-iron tetroxide, and carbon black; waxes such as Bees wax, Japan wax, Carnauba wax, Candelilla wax, and lanolin; film-forming agents such as nitrocellulose and polyvinyl alcohol; solvents or dispersing media such as water and alcohols (e.g., ethanol); powders such as aluminum powder, talc, kaolin, zinc oxide, titanium dioxide, mica, calcium carbonate, and treated powders; plasticizers such as acetyl tributyl citrate, and dibutylphthalate; pharmaceutically active agents such as retinol palmitate, γ-orizanol, pyridoxine dipalmitate, ascorbyl dipalmitate, ergocalciferol, dl-α-tocopheryl acetate, biotin, ethinylestradiol, estrone, hydrocortisone, calcium pantothenate, ammonium glycyrrhizinate, allantoin, quaiazulene, and hinokitiol; and perfumes such as musk, civet, amber, jasmin absolute, and rose oil.

The skin treatment composition according to the present invention can be prepared in any conventional form, for example, solubilized forms such as cosmetic lotions, and emulsified forms such as liquid creams, creams, ointments, and dispersions.

Evaluation Test Results

In order to show the desired results obtained from the incorporation of the hydroquinone glycoside (I) into the skin treatment composition according to the present invention, the following evaluation tests were carried out by using arbutin in comparison with hydroquinone and, in some test, hydroquinone monocaprylate.

(1) Depigmenting Effects

The depigmenting effects of arbutin and hydroquinone were evaluated by using the inhibition rate of tyrosinase, i.e. polyphenol oxidase for forming melanin. This evaluation method is generally accepted in the art.

The tyrosinase inhibition rate was determined by using DOPA as a substrate as follows:

Preparation of Sample Solution

Aqueous sample solutions having a concentration of hydroquinone or arbutin of 150, 300, or 600 mM were prepared.

Preparation of Substrate Solution

A substrate solution was prepared by dissolving 5 mg of DOPA in 10 ml of distilled water.

Preparation of Enzyme Solution

An enzyme solution was prepared by dissolving 10 mg of tyrosinase (2000 I.U./mg, Sigma Chemical Co.) in 10 ml of distilled water.

Determination

A 0.5 ml amount of the substrate solution and 0.9 ml of 1/15M phosphate buffer solution were added to 0.05 ml of the sample. The mixture was incubated at 25° C. for 5 minutes. Then, 0.05 ml of the enzyme solution, which was previously incubated at 25° C. for 5 minutes, was added to the above-incubated sample mixture. The resultant mixture was allowed to react for 1.5 minutes. The absorbancy of the resultant reaction mixture was measured at 475 nm. The tyrosinase inhibition rate was calculated from the following equation:

$$\text{Inhibition Rate} = \frac{1 - (T - T')}{C - C'} \times 100(\%)$$

wherein
T: Absorbancy in the case of the inhibitor being added;
T': Absorbancy in the case of the inhibitor being added but the substrate not being added
C: Absorbancy in the case of the inhibitor not being added
C': Absorbancy in the case of neither the inhibitor nor the substrate being added
The results are shown in Table 1.

TABLE 1

| Concentration (mM) | Inhibition Rate (%) | |
|---|---|---|
| | Hydroquinone | Arbutin |
| 5 | 46.5 | 55.3 |
| 10 | 51.6 | 62.3 |
| 20 | 59.0 | 67.1 |

As is clear from the results shown in Table 1, the inhibition effect of arbutin is superior to that of hydroquinone.

(2) Accumulated Skin Irritation

Shaved backs of 5 albino quinea pigs were used in each case. A 50 μl amount of a 1%, 5%, or 10%, or 20% (only for arbutin) solution of hydroquinone, arbutin, or hydroquinone monocaprylate in ethanol-water (1:1) was applied to each of the shaved backs once a day for successive four days.

The occurrence of the irritation was visually evaluated every day. The results are shown in Table 2, in which the number of the guinea pigs causing the irritation is listed.

TABLE 2

| Sample | Concentration % (W/V) | Lapse of time (day) | | | |
|---|---|---|---|---|---|
| | | 1 | 2 | 3 | 4 |
| Hydroquinone | 10 | 0 | 0 | 1 | 1 |
| " | 5 | 0 | 0 | 0 | 1 |
| " | 1 | 0 | 0 | 0 | 0 |
| Arbutin | 20 | 0 | 0 | 0 | 0 |
| " | 10 | 0 | 0 | 0 | 0 |
| " | 5 | 0 | 0 | 0 | 0 |
| " | 1 | 0 | 0 | 0 | 0 |
| Hydroquinone monocaprylate | 10 | 2 | 3 | 5 | 5 |
| Hydroquinone monocaprylate | 5 | 2 | 2 | 3 | 3 |
| Hydroquinone monocaprylate | 1 | 0 | 1 | 2 | 2 |

As is clear from the results shown in Table 2, hydroquinone monocaprylate exhibits strong irritation, whereas arbutin exhibits no irritation even at a concentration of 20%.

(3) Contact Sensitization

Test method

The evaluation test was carried out by using hartley strain albino guinea pigs having a body weight of 370 to 420 g according to a Sato et al's method (Sato Y., Katsumura Y., Ichikawa H., Kobayashi T. et al "A Modified Technique of Guinea Pig Testing to Identity Delayed Hypersensitivity Allergens" Contact Dermatitis 7, 225–237, 1981).

The results were evaluated by observing the degree of appearance of the abnormality and rating the results according to the following criteria.

Criteria:

| Conditions | Score |
| --- | --- |
| (1) Erythema formation: | |
| no erythema | 0 |
| slight erythema | 1 |
| obvious erythema | 2 |
| strong erythema | 3 |
| strong erythema with slight eschan | 4 |
| (2) Edema: | |
| no edema | 0 |
| very slight edema | 1 |
| slight edema | 2 |
| medium edema (about 1 mm) | 3 |
| strong edema (extending beyond applied region) | 4 |

The tests were carried out by using hydroquinone, arbutin, and hydroquinone monocaprylate. The results are shown in Table 3.

TABLE 3

| Sample | Induction % | Challenge % | Results | |
| --- | --- | --- | --- | --- |
| Hydroquinone | 5 | 5 | 5/5 | 2.6 |
| Arbutin | 5 | 5 | 0/1 | 0 |
| " | 20 | 20 | 0/1 | 0 |
| Hydroquinone monocaprylato | 5 | 5 | 5/5 | 3.4 |

As is clear from the results shown in Table 3, the order of the contact sensitization potential was as follows:

Hydroquinone monocaprylate > Hydroquinone > Arbutin

Thus, it is clearly proved that the contact sensitivity of arbutin is remarkably low compared with that of other depigmenting agents.

(4) Stability with Time

Hydroquinone, arbutin, or hydroquinone monocaprylate was dissolved at a concentration of 1 mM in a 0.1N aqueous sodium hydroxide solution. The changes in the color of the resultant solutions with the lapse of time at 37° C. were monitored by measuring the absorbancy at 420 nm.

The results are shown in FIG. 1. In FIG. 1, the curve (1) represents the change in color in the case of arbutin. The curves (2) and (3) represent the changes in color in the case of hydroquinone and hydroquinone monocaprylate. As is clearly shown in FIG. 1, in the case of hydroquinone the solution was rapidly colored brown, whereas in the case of hydroquinone monocaprylate the stability was improved moderate. However, in the case of arbutin, the change of appearance was not observed.

In order to confirm the stability of the actual formula, the stability tests were carried out by using the neutral cream obtained in the below-mentioned Example 8 and two samples in which the arbutin in Example 8 was replaced by hydroquinone and hydroquinone monocaprylate, respectively.

These three samples were stored at a temperature of 37° C. for 1 month, 2 months, and 3 months. The degrees of the discoloration of these samples were as shown in Table 4.

TABLE 4

| | Storage Period (month) | | |
| --- | --- | --- | --- |
| Sample | 1 | 2 | 3 |
| Hydroquinone | − | − − | − − |
| Hydroquinone monocaprylate | + | + | − |
| Arbutin | + + | + + | + + |

+ +: Not changed in appearnce
+: Slightly changed brown
−: Moderately changed brown
− −: Conspicuously changed brown As is clear from the results shown in Table 4, the stability of arbutin with the lapse of time is excellent.

EXAMPLES

The present invention will now be further illustrated by, but is by no means limited to, the following Examples, wherein "percents" are all by weight unless otherwise specified.

EXAMPLE 1: PREPARATION OF NEUTRAL CREAM

| Ingredient | % |
| --- | --- |
| Stearyl alcohol | 7.0 |
| Stearic acid | 2.0 |
| Hydrogenated lanolin | 2.0 |
| Squalane | 5.0 |
| 2-Octyldodecyl alcohol | 6.0 |
| Polyoxyethylene (25 moles) cetyl alcohol ether | 3.0 |
| Glycerol monostearate | 2.0 |
| Propylene glycol | 5.0 |
| Arbutin* | 10.0 |
| Perfume | q.s. |
| Preservative | q.s. |
| Anti-oxidant | q.s. |
| De-ionized water | Balance |

*available from WAKO JUNYAKU K. K., JAPAN

The arbutin and propylene glycol were added to the de-ionized water. The mixture was heated and maintained at a temperature of 70° C. (i.e., aqueous phase). The other ingredients were mixed together to melt upon heating and maintained at a temperature of 70° C. (i.e., oily phase).

The oily phase obtained above was added to the aqueous phase and, after pre-emulsification, the mixture was homogeneously emulsified in a homomixer. The emulsified product was cooled, while stirring, after the emulsification.

EXAMPLE 2: PREPARATION OF LIQUID CREAM

| Ingredient | % |
| --- | --- |
| Stearic acid | 2.5 |
| Cetyl alcohol | 1.5 |
| Vaseline | 5.0 |
| Liquid paraffin | 10.0 |
| Polyoxyethylene (10 moles) monooleate | 2.0 |
| Polyethylene glycol 1500 | 3.0 |
| Triethanolamine | 1.0 |
| Arbutin | 20.0 |
| Perfume | q.s. |
| Preservative | q.s. |
| Anti-oxidant | q.s. |
| De-ionized water | Balance |

The arbutin, polyethylene glycol, and triethanolamine were added to the de-ionized water. The mixture was dissolved upon heating add maintained at a temperature of 70° C. (i.e., aqueous phase). The other ingredients were mixed together to melt upon heating and maintained at a temperature of 70° C. (i.e., oily phase).

The oily phase obtained above was added to the aqueous phase and, after pre-emulsification, the mixture was homogeneously emulsified in a homomixer. The emulsified product was cooled to a temperature of 20° C., while stirring, after the emulsification.

EXAMPLE 3: PREPARATION OF JELLY

| Ingredient | % |
|---|---|
| 95% ethanol | 25.0 |
| Dipropylene glycol | 15.0 |
| Polyoxyethylene (15 moles) oleyl alcohol ether | 2.0 |
| Carboxyvinylpolymer (Trade mark: Carbomer 941) | 1.0 |
| Potassium hydroxide | 0.15 |
| L-arginine | 0.1 |
| Arbutin | 30.0 |
| Perfume | q.s. |
| Preservative | q.s. |
| De-ionized water | Balance |

The arbutin and carboxyvinylpolymer were homogeneously dissolved in the de-ionized water to form an aqueous solution. On the other hand, the dipropylene glycol, polyoxyethylene (15 moles) oleyl alcohol ether, perfume, and preservative were dissolved in 95% ethanol and the resultant ethanol solution was added to the aqueous solution. The aqueous phase thus prepared was neutralized and thickened with potassium hydroxide and L-arginine.

EXAMPLE 4: PREPARATION OF POWDER-CONTAINING PACK

| Ingredient | % |
|---|---|
| Alcohol phase | |
| 95% Ethanol | 2.0 |
| Preservative | q.s. |
| Perfume | q.s. |
| Colorant | q.s. |
| Aqueous phase | |
| Arbutin | 7.0 |
| Propylene glycol | 7.0 |
| Zinc oxide | 25.0 |
| Kaolin | 20.0 |
| De-ionized water | Balance |

The aqueous phase was homogeneously prepared at room temperature. Then, the alcohol phase previously prepared was added to the aqueous phase and mixed homogeneously.

EXAMPLE 5: PREPARATION OF WATER ABSORPTION OINTMENT

| Ingredient | % |
|---|---|
| Vaseline | 40.0 |
| Stearyl alcohol | 18.0 |
| Japan wax | 20.0 |
| Polyoxyethylene (10 moles) monooleate | 0.25 |
| Glycerol monostearate | 0.25 |
| Arbutin | 10.0 |
| De-ionized water | Balance |

The arbutin was added to the de-ionized water. The mixture was heated and maintained at a temperature of 70° C. (i.e., aqueous phase). The other ingredients were mixed together to melt upon heating and maintained at a temperature of 70° C. (i.e., oily phase).

The oily phase obtained above was added to the aqueous phase and, after pre-emulsification, the mixture was homogeneously emulsified in a homomixer. The emulsified product was cooled, while stirring, after the emulsification.

EXAMPLE 6: PREPARATION OF VANISHING CREAM

| Ingredient | % |
|---|---|
| Stearic acid | 5.0 |
| Stearyl alcohol | 4.0 |
| Butyl stearate | 8.0 |
| Glycerol monostearate | 2.0 |
| Methyl-2,5-diisopropyl cinnamate (UV absorber) | 5.0 |
| Propylene glycol | 10.0 |
| Arbutin | 1.0 |
| Potassium hydroxide | 0.2 |
| Preservative | q.s. |
| Anti-oxidant | q.s. |
| Perfume | q.s. |
| De-ionized water | Balance |

The arbutin, propylene glycol, and potassium hydroxide were added to the de-ionized water. The mixture was heated and maintained at a temperature of 70° C. (i.e., aqueous phase). The other ingredients were mixed together to melt upon heating and maintained at a temperature of 70° C. (i.e., oily phase).

The oily phase obtained above was gradually added to the aqueous phase. After allowing to stand at the same temperature for a while, the mixture was homogeneously emulsified in a homomixer. The emulsified product was cooled to a temperature of 30° C., while stirring.

EXAMPLE 7: PREPARATION OF VANISHING CREAM

| Ingredient | % |
|---|---|
| Stearic acid | 6.0 |
| Sorbitan monostearate | 2.0 |
| Polyoxyethylene (20 moles) sorbitan monostearate | 1.5 |
| 2-(2'-Hydroxy-5'-methylphenyl) benzotriazole (UV absorber) | 8.0 |
| Propylene glycol | 10.0 |
| Hydroquinone-$\beta$-L-arabinoside | 5.0 |
| Preservative | q.s. |
| Anti-oxidant | q.s. |
| Perfume | q.s. |
| De-ionized water | Balance |

The hydroquinone-$\beta$-L-arabinoside and propylene glycol were added to the de-ionized water. The mixture was heated and maintained at a temperature of 70° C. (i.e., aqueous phase). The other ingredients were mixed together to melt upon heating and maintained at a temperature of 70° C. (i.e., oily phase).

The oily phase obtained above was added to the aqueous phase and after pre-emulsification, the mixture was homogeneously emulsified in a homomixer. The emulsified product was cooled to a temperature of 30° C., while stirring, after the emulsification.

EXAMPLE 8: PREPARATION OF NEUTRAL CREAM

| Ingredient | % |
|---|---|
| Stearyl alcohol | 7.0 |
| Stearic acid | 2.0 |
| Hydrogenated lanolin | 2.0 |
| Squalane | 5.0 |
| 2-Octyldodecyldodecyl alcohol | 6.0 |
| Polyoxyethylene (25 moles) cetyl alcohol ether | 3.0 |
| Glycerol monostearate | 2.0 |
| Octyl ester of N,N-dimethyl PABA (UV absorber) | 3.0 |
| Propylene glycol | 5.0 |
| Arbutin | 10.0 |
| Perfume | q.s. |
| Preservative | q.s. |
| Anti-oxidant | q.s. |
| De-ionized water | Balance |

The arbutin and propylene glycol were added to the de-ionized water. The mixture was heated and maintained at a temperature of 70° C. (i.e., aqueous phase). The other ingredients were mixed together to melt upon heating and maintained at a temperature of 70° C. (i.e., oily phase).

The oily phase obtained above was added to the aqueous phase and, after pre-emulsification, the mixture was homogeneously emulsified in a homomixer. The emulsified product was cooled, while stirring, after the emulsification.

EXAMPLE 9: PREPARATION OF COLD CREAM

| Ingredient | % |
|---|---|
| Solid paraffin | 5.0 |
| Beeswax | 10.0 |
| Vaseline | 15.0 |
| Liquid paraffin | 41.0 |
| Glycerol monostearate | 2.0 |
| Polyoxyethylene (20 moles) sorbitan monolaurate | 2.0 |
| 4-Methoxy-4'-t-butyl dibenzoyl methane (UV absorber) | 3.0 |
| Soap powder | 0.1 |
| Borax | 0.2 |
| Arbutin | 3.0 |
| Perfume | q.s. |
| Preservative | q.s. |
| Anti-oxidant | q.s. |
| De-ionized water | Balance |

The arbutin, soap powder, and borax were added to the de-ionized water. The mixture was dissolved upon heating and maintained at a temperature of 70° C. (i.e., aqueous phase). The other ingredients were mixed together to melt upon heating and maintained at a temperature of 70° C. (i.e., oily phase).

The oily phase obtained above was added to the aqueous phase and, after pre-emulsification, the mixture was homogeneously emulsified in a homomixer. The emulsified product was cooled to a temperature of 30° C., while stirring, after the emulsification.

EXAMPLE 10: PREPARATION OF LIQUID CREAM

| Ingredient | % |
|---|---|
| Polyoxyethylene (20 moles) polyoxypropylene (2 moles) cetyl alcohol | 1.0 |
| Silicone KF96 (20 cs, available from Shinetsu Kagaku) | 2.0 |
| Liquid paraffin (medium viscosity) | 3.0 |
| Octyl ester of N,N-dimethyl PABA (UV absorber) | 5.0 |
| Propylene glycol | 5.0 |
| Glycerol | 2.0 |
| Ethyl alcohol | 15.0 |
| Carboxy vinyl polymer | 0.3 |
| Hydroxypropyl cellulose | 0.1 |
| 2-aminomethyl propanol | 0.1 |
| Arbutin | 3.0 |
| Preservative | q.s. |
| De-ionized water | Balance |

The arbutin was dissolved, upon heating, in the ethyl alcohol and de-ionized water. Further, the other water-soluble ingredients including the propylene glycol were dissolved in the aqueous mixture (i.e., aqueous phase). The other ingredients were mixed together to melt upon heating and maintained at a temperature of 70° C. (i.e., oily phase).

The oily phase obtained above was added to the aqueous phase and, after pre-emulsification, the mixture was homogeneously emulsified in a homomixer. The emulsified product was cooled to a temperature of 30° C., while stirring, after the emulsification.

EXAMPLE 11: PREPARATION OF LIQUID CREAM

| Ingredient | % |
|---|---|
| Polyoxyethylene (20 moles) polyoxypropylene (2 moles) cetyl alcohol | 1.0 |
| Silicone KF96 (20 cs, available from Shinetsu Kagaku) | 2.0 |
| Liquid paraffin (medium viscosity) | 3.0 |
| Octyl ester of N,N-dimethyl PABA (UV absorber) | 5.0 |
| Propylene glycol | 5.0 |
| Glycerol | 2.0 |
| Ethyl alcohol | 15.0 |
| Carboxy vinyl polymer | 0.3 |
| Hydroxypropyl cellulose | 0.1 |
| 2-aminomethyl propanol | 0.1 |
| Arbutin | 7.0 |
| Preservative | q.s. |
| De-ionized water | Balance |

The arbutin was dissolved, upon heating, in the ethyl alcohol and de-ionized water. Further, the other water-soluble ingredients including the propylene glycol were dissolved in the aqueous mixture (i.e., aqueous phase). The other ingredients were mixed together to melt upon heating and maintained at a temperature of 70° C. (i.e., oily phase).

The oily phase obtained above was added to the aqueous phase and, after pre-emulsification, the mixture was homogeneously emulsified in a homomixer. The emulsified product was cooled to a temperature of 30° C., while stirring, after the emulsification.

EXAMPLE 12: PREPARATION OF LIQUID CREAM

| Ingredient | % |
|---|---|
| Polyoxyethylene (20 moles) polyoxypropylene (2 moles) cetyl alcohol | 1.0 |
| Silicone KF96 (20 cs, available from | 2.0 |

-continued

| Ingredient | % |
|---|---|
| Shinetsu Kagaku) | |
| Liquid paraffin (medium viscosity) | 3.0 |
| Octyl ester of N,N-dimethyl PABA (UV absorber) | 5.0 |
| Propylene glycol | 5.0 |
| Glycerol | 2.0 |
| Ethyl alcohol | 15.0 |
| Carboxy vinyl polymer | 0.3 |
| Hydroxypropyl cellulose | 0.1 |
| 2-aminomethyl propanol | 0.1 |
| Arbutin | 20.0 |
| Preservative | q.s. |
| De-ionized water | Balance |

The arbutin was dissolved, upon heating, in the ethyl alcohol and de-ionized water. Further, the other water-soluble ingredients including the propylene glycol were dissolved in the aqueous mixture (i.e., aqueous phase). The other ingredients were mixed together to melt upon heating and maintained at a temperature of 70° C. (i.e., oily phase).

The oily phase obtained above was added to the aqueous phase and, after pre-emulsification, the mixture was homogeneously emulsified in a homomixer. The emulsified product was cooled to a temperature of 30° C., while stirring, after the emulsification.

EXAMPLE 13: PREPARATION OF LIQUID CREAM

| Ingredient | % |
|---|---|
| Stearic acid | 1.5 |
| Cetyl alcohol | 0.5 |
| Beeswax | 2.0 |
| Polyoxygethylene (20 moles) monooleate | 1.0 |
| Glycerol monostearate | 1.0 |
| Quince seed extract (5% aqueous solution) | 20.0 |
| Propylene glycol | 5.0 |
| Octyl ester of N,N-dimethyl PABA (UV absorber) | 5.0 |
| Perfume | q.s. |
| Preservative | q.s. |
| Anti-oxidant | q.s. |
| Ethyl alcohol | 10.0 |
| Arbutin | 0.1 |
| De-ionized water | Balance |

The arbutin and propylene glycol were added to the de-ionized water. The mixture was dissolved upon heating and maintained at a temperature of 70° C. (i.e., aqueous phase). The perfume and UV absorber were dissolved in the ethyl alcohol (i.e., alcoholic phase). The other ingredients, other than the quince seed extract, were mixed and melted, upon heating, and maintained at a temperature of 70° C. (i.e., oily phase).

The oily phase was added to the aqueous phase and, after pre-emulsification, the mixture was homogeneously emulsified in a homomixer. While stirring, the alcoholic phase and the quince seed extract were added. Thereafter, the resultant mixture was cooled to a temperature of 30° C., while stirring.

EXAMPLE 14: PREPARATION OF LIQUID CREAM

| Ingredient | % |
|---|---|
| Microcrystalline wax | 1.0 |
| Beeswax | 2.0 |
| Lanolin | 2.0 |

-continued

| Ingredient | % |
|---|---|
| Liquid paraffin | 20.0 |
| Squalane | 10.0 |
| Sorbitan sesquioleate | 4.0 |
| Polyoxyethylene (20 moles) sorbitan monooleate | 1.0 |
| 4-Methoxy-4'-t-butyl dibenzoyl methane (UV absorber) | 10.0 |
| Propylene glycol | 7.0 |
| Arbutin | 2.0 |
| Perfume | q.s. |
| Preservative | q.s. |
| Anti-oxidant | q.s. |
| De-ionized water | Balance |

The arbutin and polyethylene glycol were added to the de-ionized water. The mixture was heated and maintained at a temperature of 70° C. (i.e., aqueous phase). The other ingredients, were mixed together to melt upon heating and maintained at a temperature of 70° C. (i.e., oily phase).

The oily phase obtained above was added to the aqueous phase and, after pre-emulsification, the mixture was homogeneously emulsified in a homomixer. The emulsifieid product was cooled to a temperature of 30° C., while stirring, after the emulsification.

EXAMPLE 15: PREPARATION OF COSMETIC LOTION

| Ingredient | % |
|---|---|
| (Alcohol phase) | |
| 95% ethanol | 25.0 |
| Polyoxyethylene (60 moles) hydrogenated castor oil ester | 2.0 |
| Anti-oxidant | q.s. |
| Preservative | q.s. |
| Perfume | q.s. |
| (Aqueous phase) | |
| Arbutin | 0.5 |
| Glycerol | 5.0 |
| Sodium hexametaphosphate | q.s. |
| Sodium 2-hydroxy-4-methoxybenzophenone-5-sulfonate (UV absorber) | 0.1 |
| De-ionized water | Balance |

The aqueous phase and the alcohol phase were separately prepared and solubilized.

EXAMPLE 16: PREPARATION OF JELLY

| Ingredient | % |
|---|---|
| 95% ethanol | 10.0 |
| Dipropylene glycol | 15.0 |
| Polyoxyethylene (15 moles) oleyl alcohol ether | 2.0 |
| 4-Methoxy-4'-t-butyl dibenzoyl methane (UV absorber) | 0.5 |
| Carboxyvinylpolymer (Trade mark: Carbomer 941) | 1.0 |
| Potassium hydroxide | 0.15 |
| L-arginine | 0.1 |
| Arbutin | 30.0 |
| Perfume | q.s. |
| Preservative | q.s. |
| De-ionized water | Balance |

The arbutin and carboxyvinylpolymer were homogeneously dissolved in the de-ionized water to form an aqueous solution. On the other hand, the dipropylene glycol, polyoxyethylene (15 moles) oleyl alcohol ether, perfume, and preservative were dissolved in 95% ethanol and the resultant ethanol solution was added to the aqueous solution. The aqueous phase thus prepared was neutralized and thickened with potassium hydroxide and L-arginine.

EXAMPLE 17: PREPARATION OF PEEL-OFF TYPE PACK

| Ingredient | % |
|---|---|
| (Alcohol phase) | |
| 95% ethanol | 10.0 |
| Polyoxyethylene (15 moles) oleyl alcohol ether | 2.0 |
| Glyceryl mono-2-ethylhexanoyl diparamethoxy-cinnamate (UV absorber) | 0.5 |
| Preservative | q.s. |
| Perfume | q.s. |
| (Aqueous phase) | |
| Arbutin | 3.0 |
| Polyvinyl alcohol | 12.0 |
| Glycerol | 3.0 |
| Polyethylene glycol 1500 | 1.0 |
| De-ionized water | Balance |

The aqueous phase was prepared at a temperature of 80° C. and then cooled to a temperature of 50° C. The alcoholic phase separately prepared at room temperature was then added to the aqueous phase. The mixture was homogeneously mixed and was allowed to cool under ambient conditions.

EXAMPLE 18: PREPARATION OF POWDER-CONTAINING PACK

| Ingredient | % |
|---|---|
| Alcohol phase | |
| 95% Ethanol | 2.0 |
| Preservative | q.s. |
| Perfume | q.s. |
| Colorant | q.s. |
| 4-Methoxy-4'-t-butyl dibenzoylmethane | 10.0 |
| Aqueous phase | |
| Arbutin | 7.0 |
| Propylene glycol | 7.0 |
| Zinc oxide | 25.0 |
| Kaolin | 20.0 |
| De-ionized water | Balance |

The aqueous phase was homogeneously prepared at room temperature. Then, the alcohol phase previously prepared was added to the aqueous phase and mixed homogeneously.

EXAMPLE 19: PREPARATION OF WATER ABSORPTION

| Ointment Ingredient | % |
|---|---|
| Vaseline | 40.0 |
| Stearyl alcohol | 18.0 |
| Japan wax | 20.0 |
| Polyoxyethylene (10 mole) monooleate | 0.25 |
| Glycerol monostearate | 0.25 |
| Arbutin | 10.0 |
| Octyl ester of N,N-dimethyl PABA (UV absorber) | 1.0 |
| De-ionized water | balance |

The arbutin was added to the de-ionized water. The mixture was heated and maintained at a temperature of 70° C. (i.e., aqueous phase). The other ingredients were mixed together to melt upon heating and maintained at a temperature of 70° C. (i.e., oily phase).

The oily phase obtained above was added to the aqueous phase and, after pre-emulsification, the mixture was homogeneously emulsified in a homomixer. The emulsified product was cooled, while stirring, after the emulsification.

The skin treatment compositions prepared in the above-mentioned Examples 1 to 19 had excellent depigmenting effects, no substantial skin irritation and sensitization, and high stability with the lapse of time.

Of these, the depigmenting test results of the liquid creams prepared in Examples 10 to 12 as well as the skin irritation suffering test results of the liquid creams prepared in Examples 10 and 12 will now be explained below.

EVALUATION TEST RESULTS

(1) Depigmenting Effect

The depigmenting effects of the liquid cream samples prepared in Examples 10 to 12 were evaluated by applying these samples to 60 women having chloasma or liver spots. The women were divided into 3 groups each composed of 20 members and each sample was applied to each group. As a control, a liquid cream, which was prepared in the same manner as in Example 10 except that no arbutin was added, was used.

The sample was applied to the affected part twice a day for 12 weeks in an amount of 0.2 to 0.3 g per each time. The improvements in the affected parts were visually observed after 12 weeks.

The results are shown in Table 5.

TABLE 5

| Classification*[1] | Example 10 Number (Improvement %) | Example 11 Number (Improvement %) | Example 12 Number (Improvement %) | Control Number (Improvement %) |
|---|---|---|---|---|
| ++++ | 0 | 0 | 0 | 0 |
| +++ | 0 | 1 (5) | 4 (20) | 0 |
| ++ | 1 (5.0) | 4 (20) | 10 (50) | 0 |
| + | 5 (25.0) | 9 (45) | 5 (25) | 3 (15) |
| ± | 14 (70.0) | 6 (30) | 1 (5) | 17 (85) |
| — | 0 | 0 | 0 | 0 |
| Total | 20 | 20 | 20 | 20 |

*[1]:
++++ Pigment deposition disappeared
+++ Remarkably improved
++ Substantially improved
+ A little improved
± Unchanged
— Turned worse

(2) Skin Irritation Suffering Effect

The skin irritation suffering effects of arbutin on the skin irritation (i.e., smarting feeling) caused by the UV absorber were evaluated by using the liquid cream samples prepared in Examples 10 and 12. As a control, a liquid cream sample, which was prepared in the same manner as in Example 10, except that no arbutin was added, was used.

The sample of Example 10 or 12 was applied to one side face of 30 women aged 19 to 26 and the control sample was applied to the other side face in an amount of 0.3 to 0.4 g per each time. The women played tennis for 2 hours outside in a summer day. Thus, the smarting feeling in the face during perspiration was organoleptically evaluated.

The results are shown in Table 6.

TABLE 6

| Degree of smarting*[1] feeling | Example 10 Number (Rate %) | Example 12 Number (Rate %) | Control Number (Rate %) |
| --- | --- | --- | --- |
| 0   | 7 (70) | 9 (90) | 1 (10) |
| ±   | 2 (20) | 1 (10) | 1 (10) |
| +   | 1 (10) | 0      | 2 (20) |
| ++  | 0      | 0      | 6 (60) |
| Total | 10   | 10     | 10     |

*[1]:
0 No feeling
± Slight feeling
+ Moderate feeling
++ Strong feeling

We claim:

1. A skin treatment composition comprising 10% to 20% by weight of a glycoside of hydroquinone having the formula

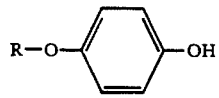 (I)

wherein R represents a pentose residue, a hexose residue, an amino sugar residue, or an uronic acid residue, or the methylated product thereof in a skin treatment base comprising 0 to 35% by weight of an alcohol, 0.01% to 5% by weight of a surfactant, 0 to 10% by weight of oil, and water or wax.

2. A skin treatment composition as claimed in claim 1, wherein the compound (I) is arbutin or hydroquinone-beta-L-arabinoside.

3. A method for depigmenting the skin comprising applying thereto an effective amount of a skin treatment composition according to claim 1.

* * * * *